United States Patent
Tseng et al.

(10) Patent No.: US 10,148,857 B2
(45) Date of Patent: Dec. 4, 2018

(54) ELECTRONIC DEVICE AND METHOD FOR SENSING TOUCH FORCE

(71) Applicant: MediaTek Inc., Hsin-Chu (TW)

(72) Inventors: Kui-Chang Tseng, Kaohsiung (TW); Tsu-Ming Liu, Hsinchu (TW)

(73) Assignee: MEDIATEK INC., Hsin-Chu (TW)

( * ) Notice: Subject to any disclaimer, the term of this patent is extended or adjusted under 35 U.S.C. 154(b) by 16 days.

(21) Appl. No.: 15/003,987

(22) Filed: Jan. 22, 2016

(65) Prior Publication Data
US 2016/0239134 A1   Aug. 18, 2016

Related U.S. Application Data

(60) Provisional application No. 62/116,710, filed on Feb. 16, 2015.

(51) Int. Cl.
| | |
|---|---|
| *G06F 3/041* | (2006.01) |
| *G06F 3/0484* | (2013.01) |
| *H04N 5/225* | (2006.01) |
| *H04N 7/14* | (2006.01) |
| *G06F 3/0488* | (2013.01) |

(Continued)

(52) U.S. Cl.
CPC ....... *H04N 5/2252* (2013.01); *G01N 15/1434* (2013.01); *G01N 21/53* (2013.01); *G01N 21/55* (2013.01); *G06F 1/1626* (2013.01); *G06F 1/1686* (2013.01); *G06F 3/016* (2013.01); *G06F 3/0414* (2013.01); *G06F 3/0416* (2013.01); *G06F 3/0484* (2013.01); *G06F 3/0488* (2013.01); *G06F 3/16* (2013.01); *G06K 9/00255* (2013.01); *G06T 3/60* (2013.01); *H04M 1/0264* (2013.01); *H04N 5/2253* (2013.01); *H04N 5/2254* (2013.01); *H04N 5/2257* (2013.01); *H04N 7/144* (2013.01); *H04N 7/15* (2013.01); *G01N 2201/062* (2013.01); *G01N 2201/0638* (2013.01); *G06F 2203/04806* (2013.01); *G06F 2203/04808* (2013.01); *H04N 2007/145* (2013.01)

(58) Field of Classification Search
CPC ......... G06F 3/0414; G06F 2203/04806; G06F 1/1626
See application file for complete search history.

(56) References Cited

U.S. PATENT DOCUMENTS

| | | | | |
|---|---|---|---|---|
| 9,250,754 B2* | 2/2016 | Tenuta | ................... | G06F 3/0414 |
| 2002/0014356 A1* | 2/2002 | Cech | ...................... | B60N 2/002 177/144 |

(Continued)

*Primary Examiner* — Amr Awad
*Assistant Examiner* — Stephen Bray
(74) *Attorney, Agent, or Firm* — McClure, Qualey & Rodack, LLP (57) ABSTRACT

An electronic device for sensing touch force is provided. The electronic device includes a display screen, a pressure sensor, a processor and a memory. The pressure sensor senses at least one touch force in a direction that is perpendicular to a plane of the display screen and generates at least one sensing signal responsive to the at least one touch force. The processor is coupled to the pressure sensor and the display screen. The memory is operatively coupled to the processor. The processor is configured to execute program code stored in the memory by: generating a control signal corresponding to the at least one sensing signal; and performing an operation according to the control signal.

12 Claims, 9 Drawing Sheets

(51) Int. Cl.
*G06K 9/00* (2006.01)
*G06T 3/60* (2006.01)
*H04N 7/15* (2006.01)
*G01N 15/14* (2006.01)
*G01N 21/53* (2006.01)
*G01N 21/55* (2014.01)
*G06F 3/16* (2006.01)
*G06F 3/01* (2006.01)
*G06F 1/16* (2006.01)
*H04M 1/02* (2006.01)

(56) References Cited

U.S. PATENT DOCUMENTS

2013/0257817 A1* 10/2013 Yliaho .................. G06F 3/0414
345/177
2013/0347101 A1* 12/2013 Wu ..................... G06F 3/04883
726/19
2016/0062500 A1* 3/2016 Kessler ................ G06F 3/0414
345/174
2016/0098131 A1* 4/2016 Ogata .................. G06F 1/1643
345/173

* cited by examiner

ELECTRONIC DEVICE AND METHOD FOR SENSING TOUCH FORCE

CROSS REFERENCE TO RELATED APPLICATIONS

This Application claims priority of U.S. Provisional Patent Application No. 62/116,710, filed on Feb. 16, 2015, the entirety of which is incorporated by reference herein.

BACKGROUND OF THE INVENTION

Field of the Invention

Aspects of the present invention relate generally to an electronic device and a method for sensing touch force and, more particularly, to an electronic device and a method for sensing touch force using a pressure sensor.

Description of the Related Art

Electronic devices such as cellular telephones are sometimes provided with pressure sensors. For example, a cellular telephone may be provided with a pressure sensor that is embedded in the cellular telephone. The pressure sensor may be used to measure the actual atmospheric pressure at the location of the cellular telephone, and estimate altitude for providing GPS route information.

However, in recent years, it is apparent that the altitude cannot be measured accurately using only a conventional pressure sensor because the altitude reading is susceptible to error caused by changes in temperature and barometric pressure.

Currently, touch display screens have become ubiquitous in current cellular telephones. Touch display screens eliminate the need for key pads. In one adaptation, the touch display screens are used, not only as a replacement for key pads, but as a user interface that detects user gestures on the touch display screen and translates the gestures into commands to be performed. However, the touch display screens are, conventionally, an LCD (liquid-crystal display) technology, or an LPD (light emitting polymer display) technology. The display screens are overlaid with a touch sensor, which use touch sensing technology such as capacitive, resistive, infrared, and surface acoustic wave technologies, to determine one or more points of contact with the touch display screens. The touch sensing technologies, however, receive information in two-dimensions in the plane of the display screen.

Therefore, how to apply the pressure sensor to detect three-dimensional touch information and to avoid changing the structure of an existing electronic device (e.g. a cellular telephone) has been an important subject in design of the cellular telephone.

BRIEF SUMMARY OF THE INVENTION

The following summary is illustrative only and is not intended to be limiting in any way. That is, the following summary is provided to introduce concepts, highlights, benefits and advantages of the novel and non-obvious techniques described herein. Not all, but select implementations are described further in the detailed description below. Thus, the following summary is not intended to identify essential features of the claimed subject matter, nor is it intended for use in determining the scope of the claimed subject matter.

Electronic devices and methods for sensing touch force are provided.

In a preferred embodiment, the invention is directed to an electronic device for sensing touch force is provided. The electronic device includes a display screen, a pressure sensor, a processor and a memory. The pressure sensor senses at least one touch force in a direction that is perpendicular to a plane of the display screen and generates at least one sensing signal responsive to the at least one touch force. The processor is coupled to the pressure sensor and the display screen. The memory is operatively coupled to the processor. The processor is configured to execute program code stored in the memory by: generating a control signal corresponding to the at least one sensing signal responsive to the touch force; and performing an operation according to the control signal.

In some embodiments, the pressure sensor further comprises a membrane. The membrane is used for keeping air-tightness, wherein the pressure sensor is located in the membrane.

In some embodiments, the pressure sensor is embedded inside a body of the electronic device.

In some embodiments, the pressure sensor is attached to a back shell of the electronic device.

In some embodiments, the pressure sensor is embedded between the display screen and a body of the electronic device.

In some embodiments, before generating the control signal corresponding to the at least one sensing signal, the processor further executes: discriminating one of a plurality of levels of the sensing signal; and generating the control signal corresponding to the one of the plurality of levels.

In some embodiments, the performing the operation comprises one of the following: controlling a three-dimensional (3D) depth of an object; rendering a strength of the touch force; refocusing the object; or controlling a zoom ratio of the object.

In some embodiments, before generating the control signal corresponding to the at least one sensing signal, the processor further executes: determining whether a number of times, duration of the at least one sensing signal, and strength of the at least one sensing signal satisfy one or more criteria; and generating the control signal in response to a determination that the number of times and the duration of the at least one sensing signal satisfies the one or more criteria.

In some embodiments, the performing the operation comprises one of the following: making an emergency call; unlocking the display screen; capturing an image; or performing an audio function.

In a preferred embodiment, the invention is directed to a method for sensing touch force, used in an electronic device, comprising: sensing, by a pressure sensor of the electronic device, at least one touch force in a direction that is perpendicular to a plane of a display screen of the electronic device and generating at least one sensing signal responsive to the at least one touch force; and generating, by a processor of the electronic device, a control signal corresponding to the at least one sensing signal, and performing an operation according to the control signal.

In some embodiments, the pressure sensor comprises a membrane used for keeping air-tightness, and the pressure sensor is located in the membrane.

In some embodiments, the pressure sensor is embedded inside a body of the electronic device.

In some embodiments, the pressure sensor is attached to a back shell of the electronic device.

In some embodiments, the pressure sensor is embedded between the display screen and a body of the electronic device.

In some embodiments, before generating the control signal corresponding to the at least one sensing signal, the method further executes: discriminating one of a plurality of levels of the sensing signal; and generating the control signal corresponding to the one of the plurality of levels.

In some embodiments, the performing the operation comprises one of the following: controlling a three-dimensional (3D) depth of an object; rendering a strength of the touch force; refocusing the object; or controlling a zoom ratio of the object.

In some embodiments, before generating the control signal corresponding to the at least one sensing signal, the method further executes: determining whether a number of times, duration of the at least one sensing signal, and strength of the at least one sensing signal satisfy one or more criteria; and generating the control signal in response to a determination that the number of times and the duration of the at least one sensing signal satisfies the one or more criteria.

In some embodiments, the performing the operation comprises one of the following: making an emergency call; unlocking the display screen; capturing an image; or performing an audio function.

BRIEF DESCRIPTION OF THE DRAWINGS

The accompanying drawings are included to provide a further understanding of the disclosure, and are incorporated in and constitute a part of the present disclosure. The drawings illustrate implementations of the disclosure and, together with the description, serve to explain the principles of the disclosure. It is appreciable that the drawings are not necessarily in scale as some components may be shown to be out of proportion than the size in actual implementation in order to clearly illustrate the concept of the present disclosure.

DETAILED DESCRIPTION OF THE INVENTION

Several exemplary embodiments of the present disclosure are described with reference to FIGS. 1 through 7, which generally relate to an electronic device and a method for sensing touch force. It should be understood that the following disclosure provides various embodiments as examples for implementing different features of the present disclosure. Specific examples of components and arrangements are described in the following to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various described embodiments and/or configurations.

Figure 1:
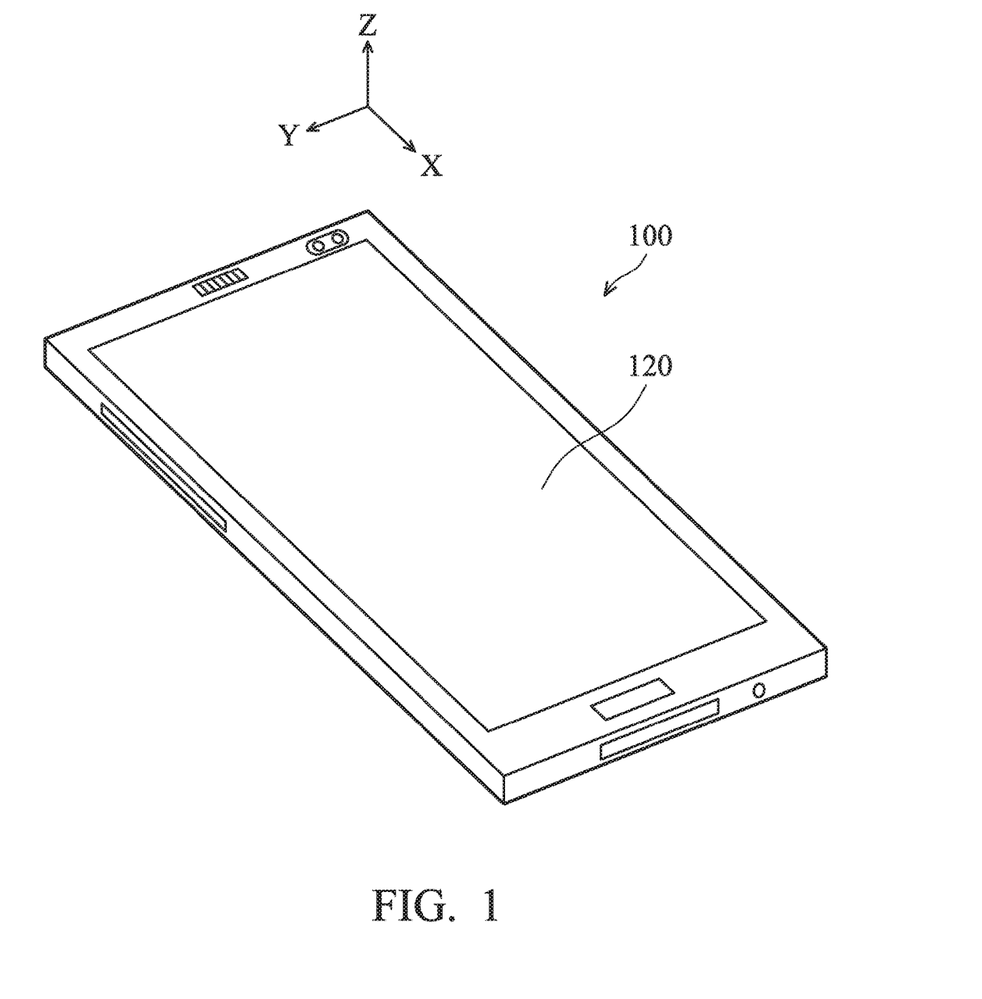
FIG. 1 is a schematic diagram illustrating an electronic device with a pressure sensor according to an embodiment of the present invention.

FIG. 1 is a schematic diagram illustrating an electronic device 100 with a pressure sensor according to an embodiment of the present invention. Electronic devices such as the electronic device 100 of FIG. 1 may be cellular telephones, media players, other handheld portable devices, somewhat smaller portable devices such as wrist-watch devices, or other wearable or miniature devices, or other electronic equipment. In some embodiments, the electronic device 100 can include a water-proof structure with an internal barometer.

Figure 2A:
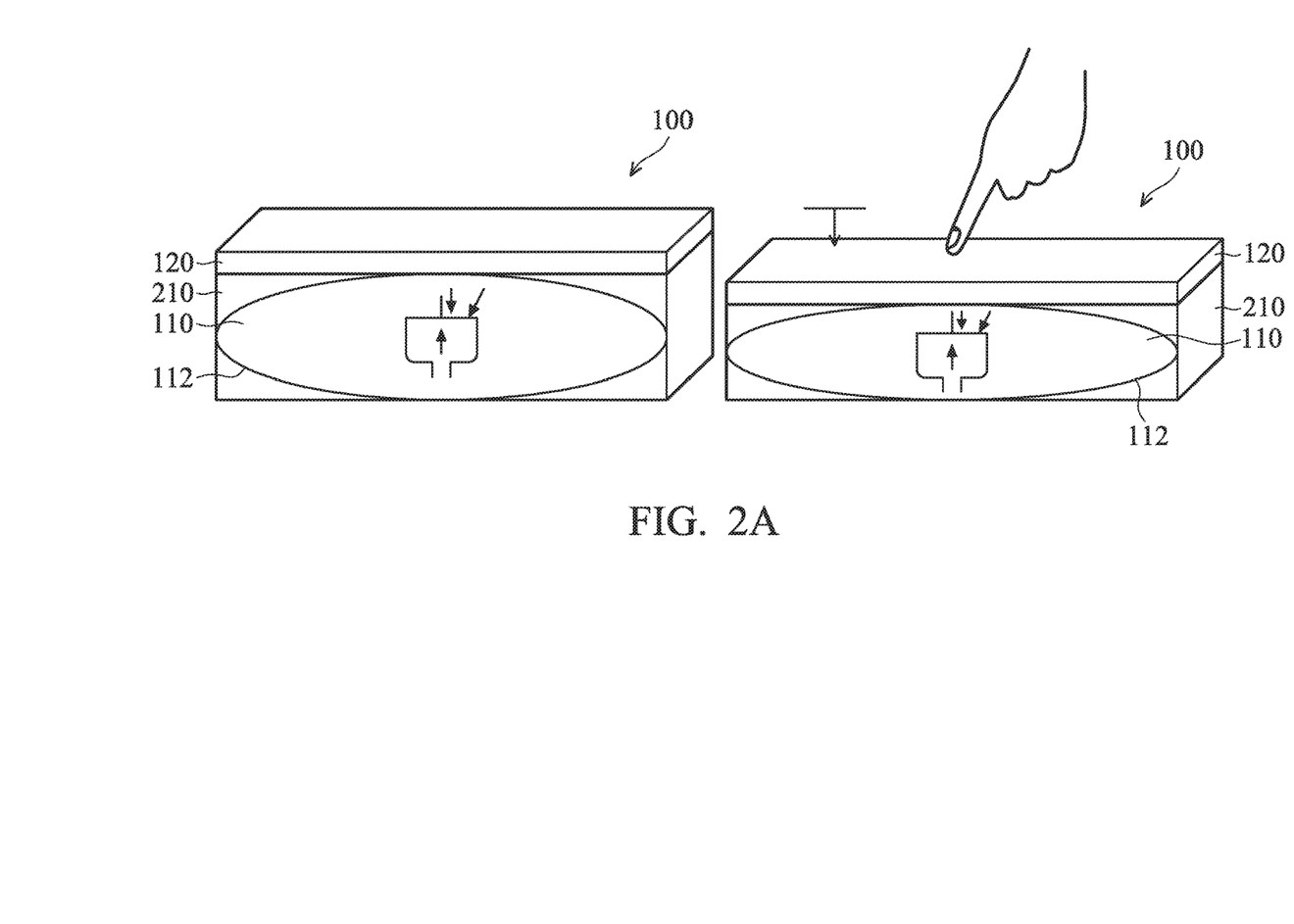
FIG. 2A is a schematic diagram illustrating that a pressure sensor is embedded inside a body of the electronic device according to an embodiment of the present invention.
Figure 2B:
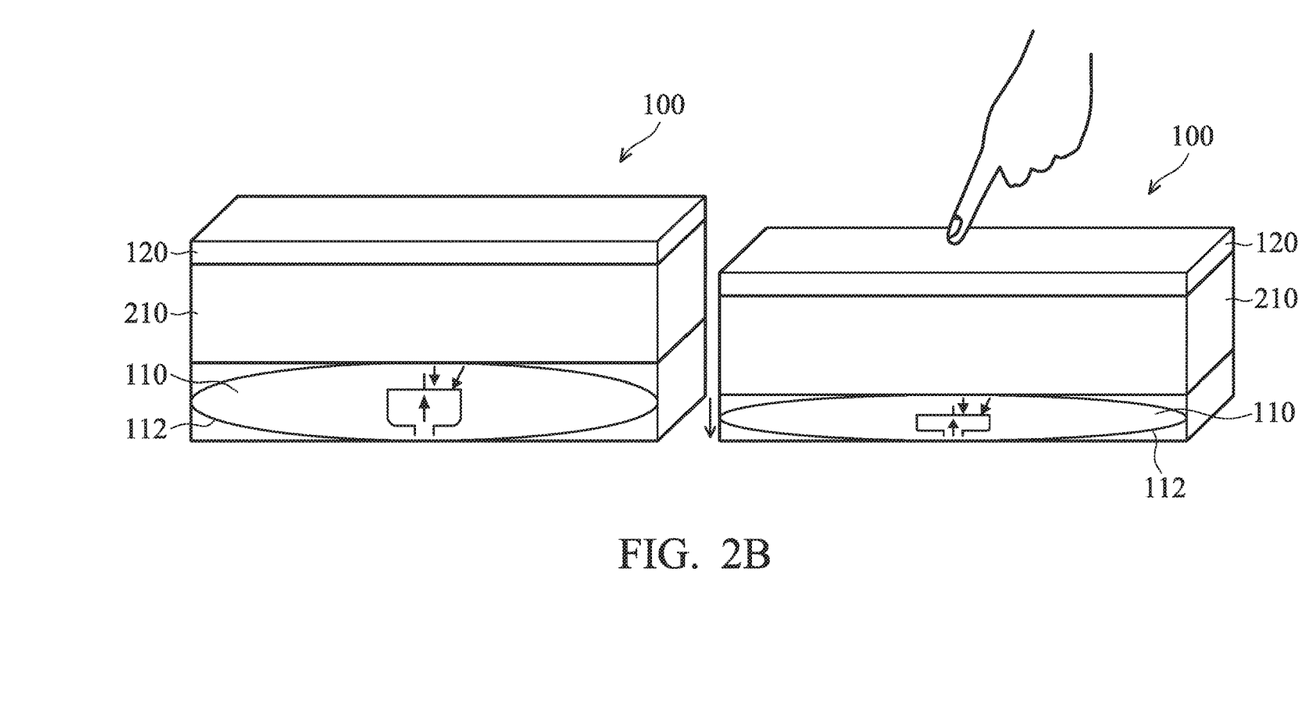
FIG. 2B is a schematic diagram illustrating that a pressure sensor is attached to a back shell of the body of the electronic device according to an embodiment of the present invention.
Figure 2C:
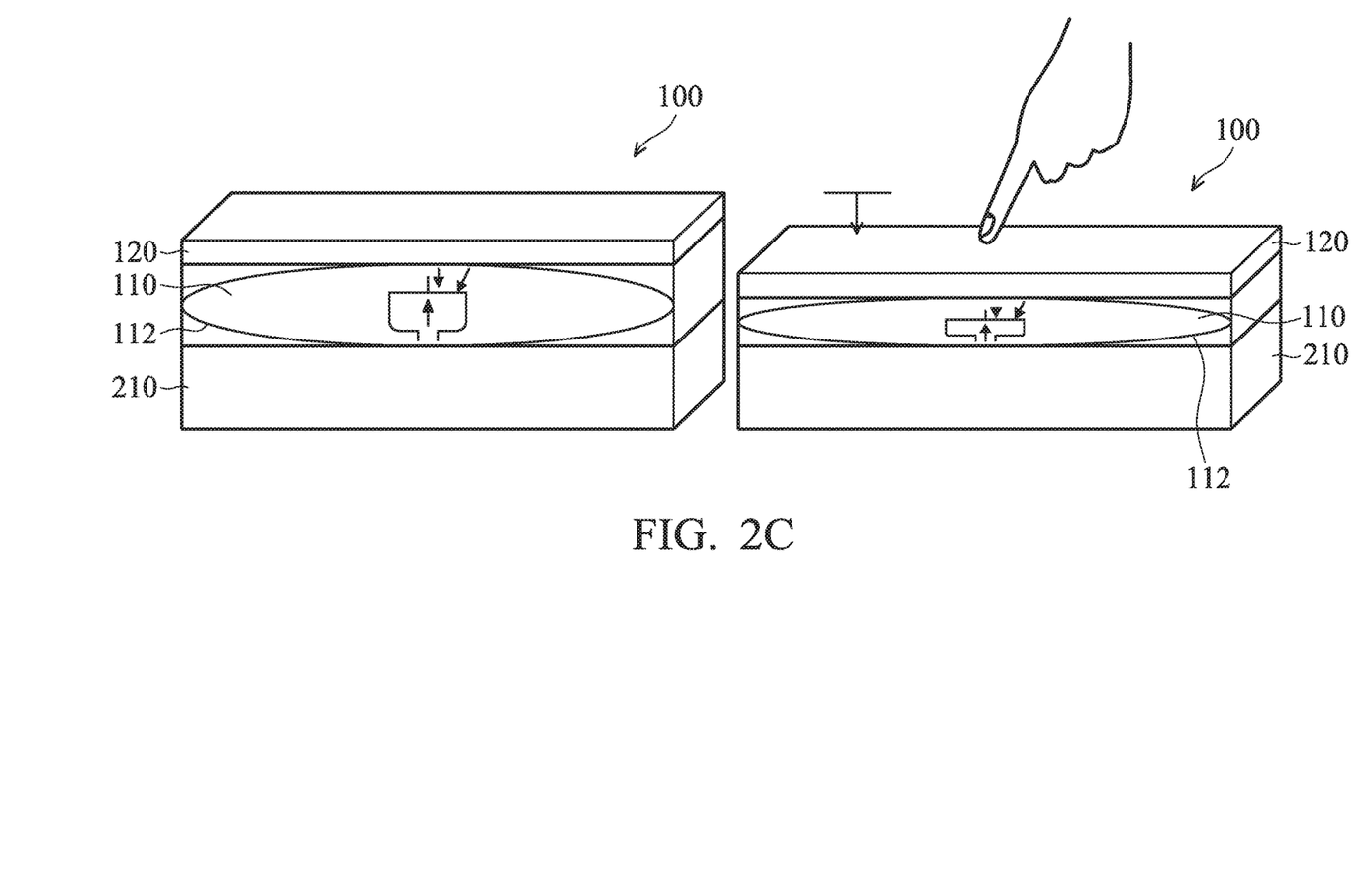
FIG. 2C is a schematic diagram illustrating that a pressure sensor is embedded between a display screen of an electronic device and a body of the electronic device according to an embodiment of the present invention.

The pressure sensor 110 can be embedded inside a body 210 of the electronic device 100, as shown in FIG. 2A. It should be noted that a display screen 120 is not included in the body 210 of the electronic device 100. Also, the pressure sensor 110 can be attached to a back shell of the body 210 of the electronic device 100, as shown in FIG. 2B. Furthermore, the pressure sensor 110 can be embedded between the display screen 120 of the electronic device 100 and the body 210 of the electronic device 100, as shown in FIG. 2C.

The pressure sensor 110 may include a membrane 112 to keep air-tightness for measurement of an absolute pressure. A pressure sensor 110 holds data of a reference pressure inside the membrane 112. The volume of the membrane 112 changes in response to a variation in a pressure of a touch force. The pressure sensor 110 is designed to calculate the pressure inside the membrane 112 based on the change in the volume. The pressure sensor 110 utilizes a difference between the reference pressure and the detected pressure to measure the pressure of the touch force. In one embodiment, the pressure sensor 110 can measure the pressure of the touch force in the Z-axis direction. As shown in FIG. 1, the X-axis of the 3D coordinate system of a display screen 120 is a horizontal direction of the display screen 120, the Y-axis of the 3D coordinate system of the display screen 120 is a vertical direction of the display screen 120, and the Z-axis of the 3D coordinate system of the display screen 120 is perpendicular to a plane of the display screen 120. It should be noted that the pressure inside the membrane 112 of the pressure sensor 110 is maintained at a constant level so as to ensure the accuracy of the measurement. Moreover, the pressure sensor 110 can be a barometer which measures an atmospheric pressure.

Figure 3:
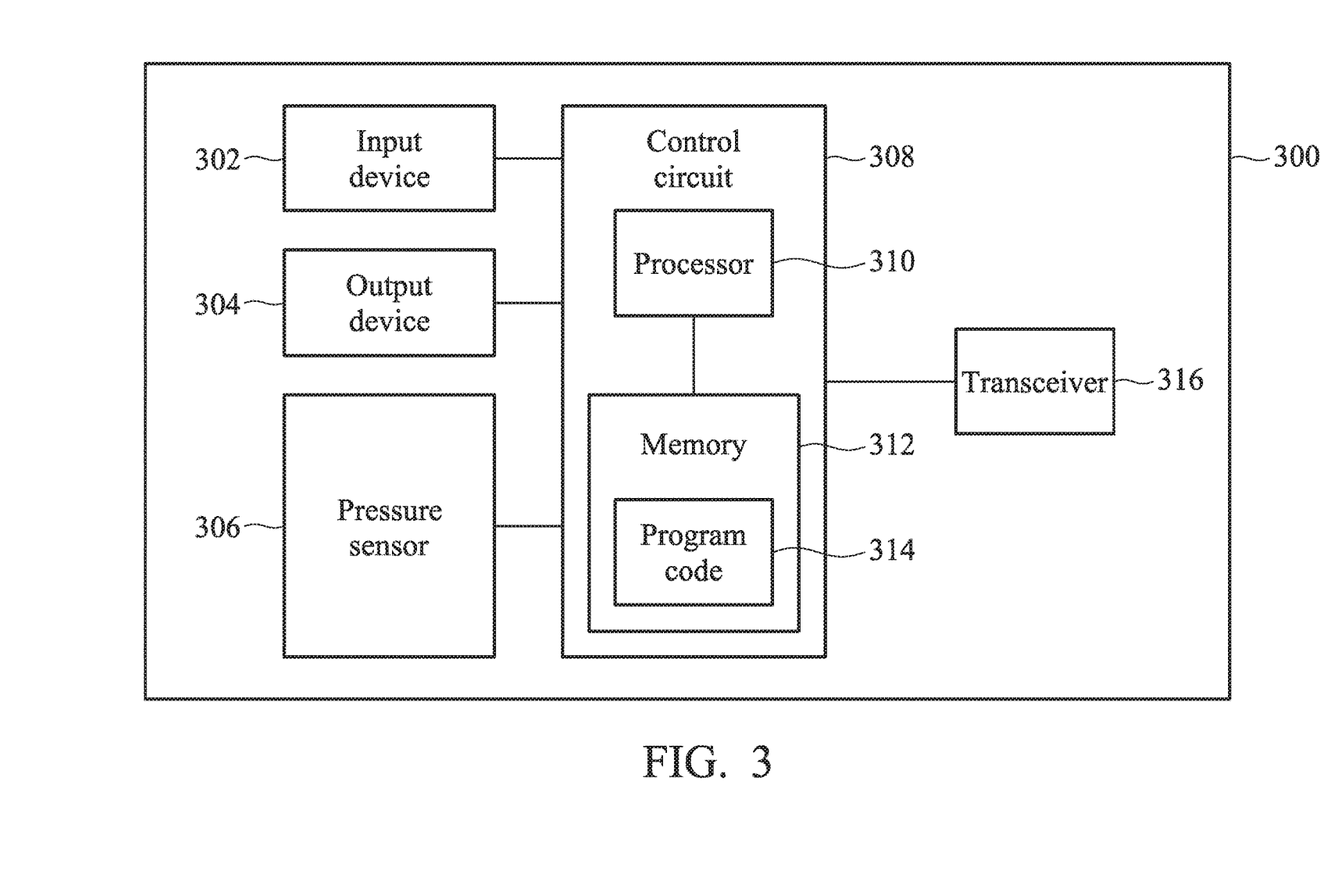
FIG. 3 is a functional block diagram of an electronic device for sensing touch force according to an embodiment of the present invention.

FIG. 3 is a functional block diagram of an electronic device 300 for sensing touch force according to an embodiment of the present invention. As shown in FIG. 3, the electronic device 300 can be utilized for realizing the electronic device 100 in FIG. 1. The electronic device 300 may include an input device 302, an output device 304, a pressure sensor 306, a control circuit 308, a processor 310, a memory 312, program code 314, and a transceiver 316.

The control circuit 308 executes the program code 314 in the memory 312 through the processor 310, thereby controlling the operation of the electronic device 300. The electronic device 300 can receive signals input by a user through the input device 302, such as a keyboard or keypad, and can output images and sounds through the output device 304, such as a display screen or speakers. The pressure sensor 306 can sense at least one touch force a direction that is substantially perpendicular to the plane of the display screen (e.g., the Z-axis direction) and generate at least one sensing signal responsive to the at least one touch force.

The transceiver 316 is used for receiving and transmitting wireless signals, delivering received signals to the control circuit 308 wirelessly, and outputting signals generated by the control circuit 308.

In one embodiment, the processor 310 may generate a control signal corresponding to the at least one sensing signal and perform an operation according to the control signal. A detailed description of this process will be described below.

Figure 4:
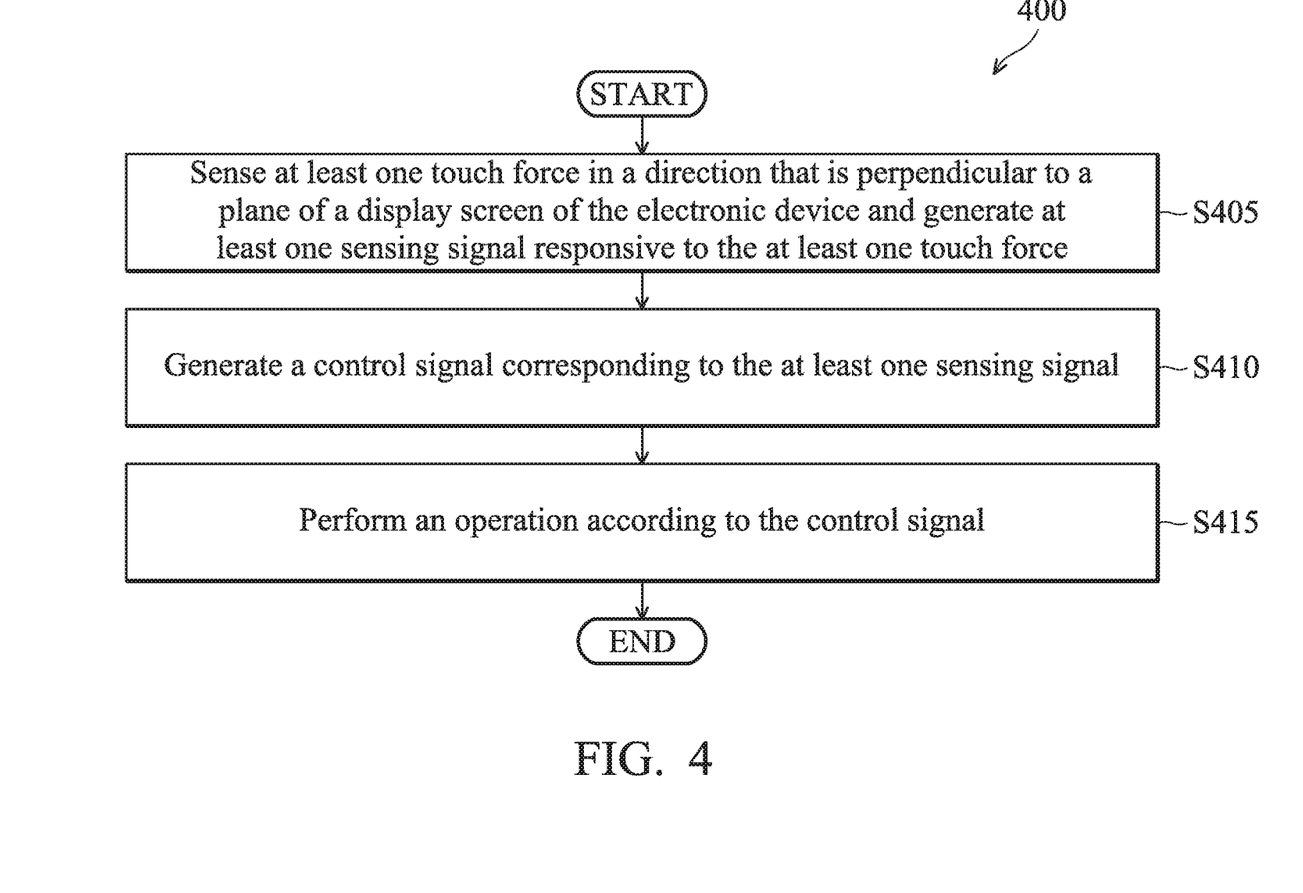
FIG. 4 is a flow diagram illustrating a method for sensing touch force according to an embodiment of the present invention with reference to FIG. 3.

FIG. 4 is a flow diagram illustrating a method 400 for sensing touch force according to an embodiment of the present invention with reference to FIG. 3. It should be noted that the method is performed by the electronic device 300 of FIG. 3. First, in step S405, the pressure sensor of the electronic device senses at least one touch force in a direction that is perpendicular to a plane of a display screen of the electronic device and generates at least one sensing signal responsive to the at least one touch force. Next, in step S410, the processor of the electronic device generates a control signal corresponding to the at least one sensing signal. In step S415, the processor of the electronic device performs an operation according to the control signal.

In one embodiment, before generating the control signal corresponding to the sensing signal in step S410, the processor may further discriminate one of a plurality of levels of the sensing signal. Then, the processor may generate the control signal corresponding to the one of the plurality of levels, wherein the levels are preferably distinguished by thresholds. The plurality of levels of the sensing signal can be stored in the memory in advance.

In the embodiment, the operation performed by the electronic device may include at least one of the following operation:
 controlling a three-dimensional (3D) depth of an object;
 rendering a strength of the touch force;
 refocusing the object; or
 controlling a zoom ratio of the object.

Figure 5A:
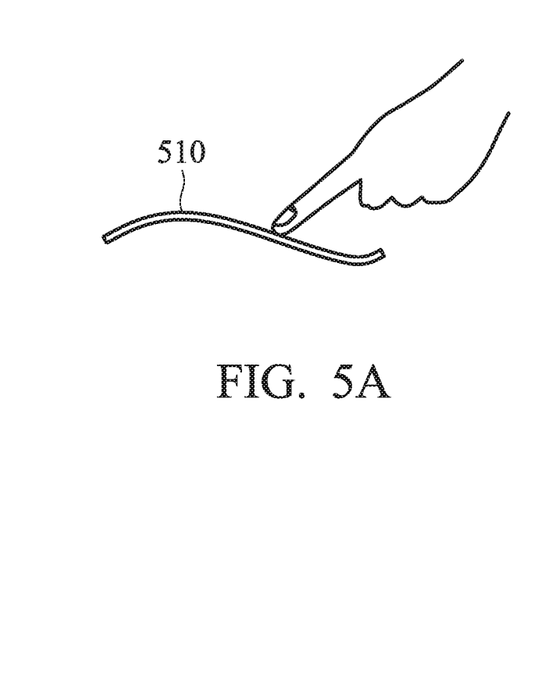
FIGS. 5A~5B are schematic views illustrating an operation performed by the electronic device according to an embodiment of the present invention.
Figure 5B:
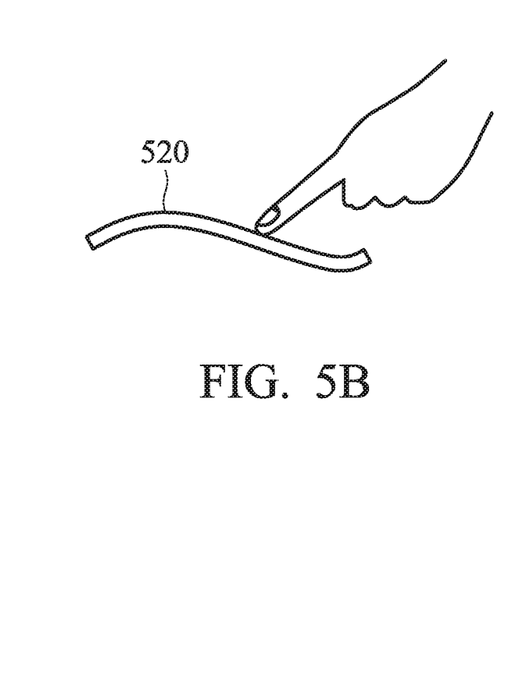

For example, FIGS. 5A~5B are schematic views illustrating an operation performed by the electronic device according to an embodiment of the present invention. As shown in FIG. 5A, the electronic device can sense a touch force and render a touch track 510 of a user on the display screen according to a plurality of levels of the sensing signal of the touch force. When the touch force in the Z-axis direction is larger than that in FIG. 5A, the touch track 520 can be rendered by using a bold line which is thicker than the touch track 510 in FIG. 5A, as shown in FIG. 5B.

Figure 6:
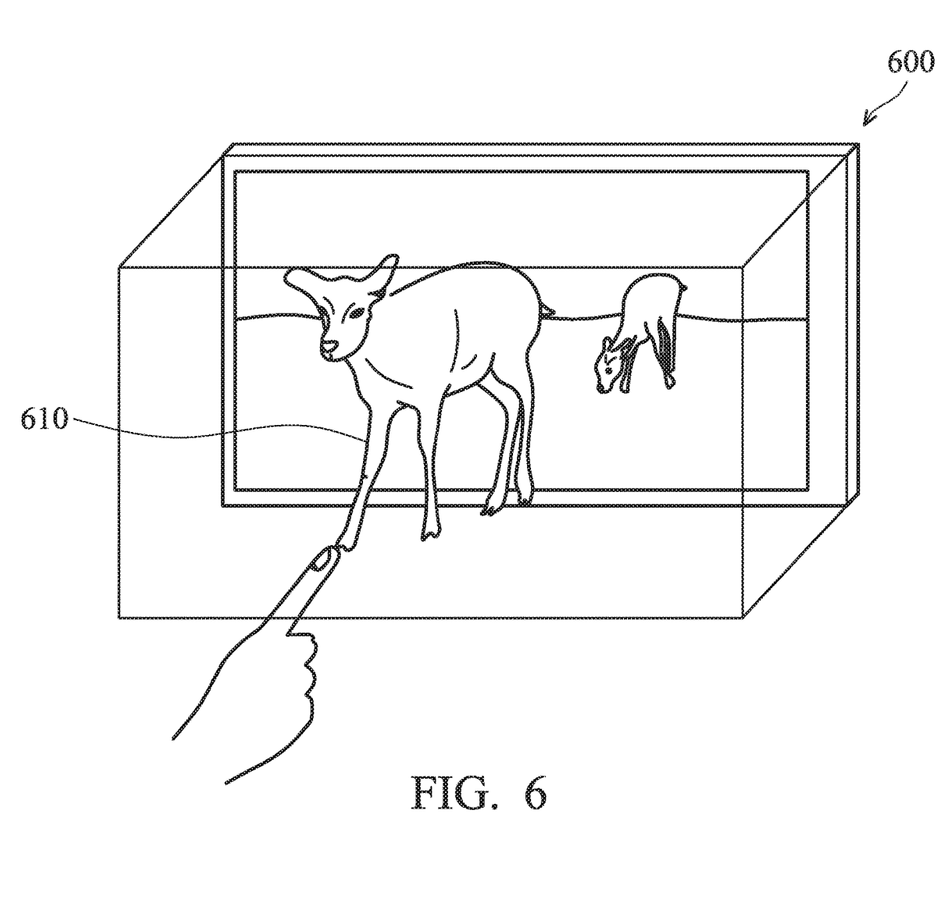
FIG. 6 is a schematic view illustrating an example for manually configuring the depth through the electronic device according to an embodiment of the present invention.

For further example, FIG. 6 is a schematic view 600 illustrating an example for manually configuring the depth through the electronic device according to embodiment of the present invention. As shown in FIG. 6, the user can select an object 610 which is a deer shape, and adjust a depth value of the object 610 according to a touch force of the user in the Z-axis direction.

Figure 7:
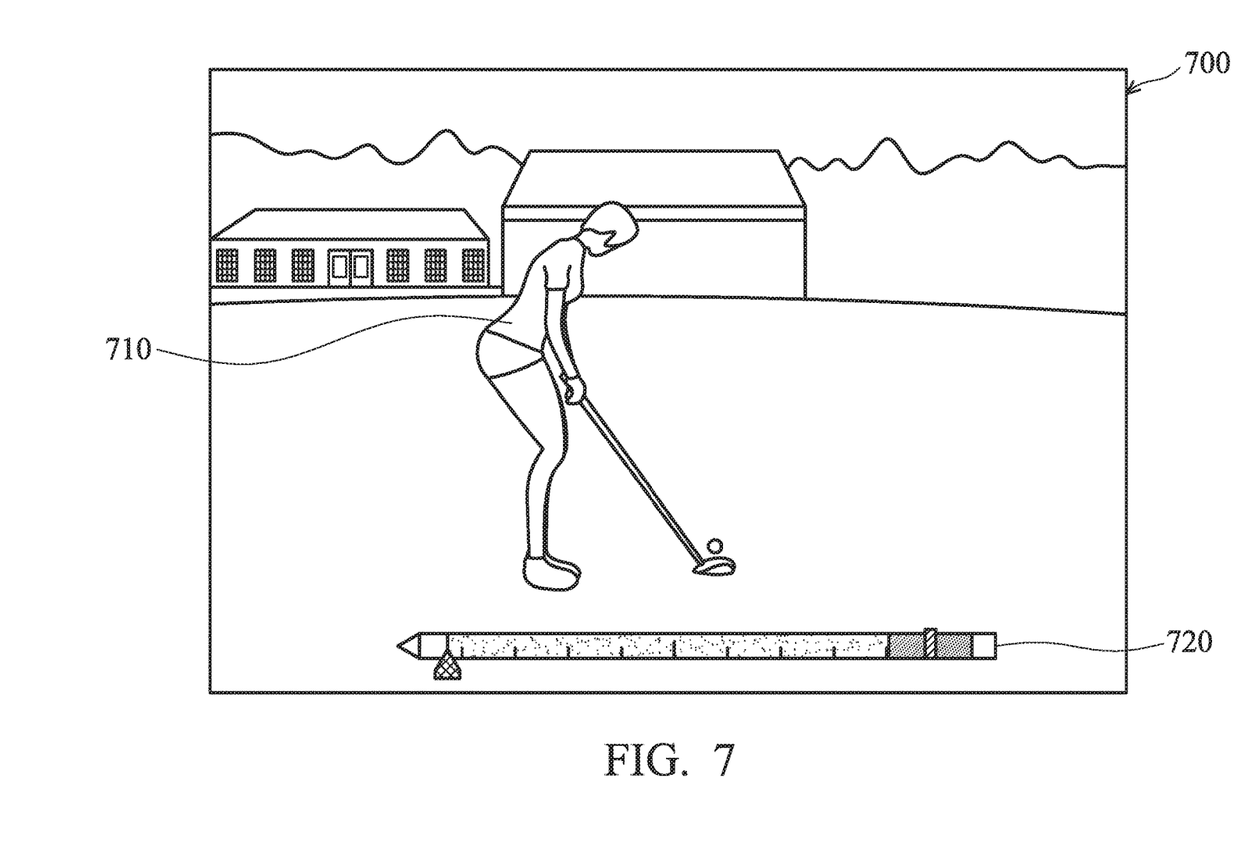
FIG. 7 is a game screen image illustrating an example for manually configuring a strength of a touch force through the electronic device according to an embodiment of the present invention.

FIG. 7 is a game screen image 700 illustrating an example for manually configuring strength of a touch force through the electronic device according to an embodiment of the present invention. On the game screen image 700, a player's character 710, and a strength bar 720 are displayed. Upon the pressure sensor senses at least one touch force in the Z-axis direction on a touch panel of the electronic device, the processor may render a strength of the touch force in the Z-axis direction through the strength bar 720.

In another embodiment, before generating the control signal corresponding to the at least one sensing signal in step S410, the processor may further determine whether a number of times and duration of the at least one sensing signal satisfies one or more criteria. Next, the processor may generate the control signal in response to a determination that the number of times, the duration of the at least one sensing signal, and strength of the at least one sensing signal satisfy the one or more criteria.

In the embodiment, the operation performed by the electronic device may include at least one of the following operation:
 making an emergency call;
 unlocking a display screen of the electronic device;
 capturing an image; or
 performing an audio function.

It should be noted that the criteria may be shown or realized in various forms such as, for example, but not limited to, the pressure sensor may generate a sensing signal responsive to a long touch, and the processor may determine whether the sensing signal maintains for longer than a predetermined time and the strength of the sensing signal responsive to the long touch in the Z-axis direction is larger than a strength threshold. Specially, in the embodiment, after the processor determines that the number of times, the duration of the at least one sensing signal, and the strength of the at least one sensing signal satisfy one or more criteria, the operations can be performed without turning on the display screen of the electronic device. Thus, the electronic device capable of dramatically improving the usability thereof can be realized.

In addition, the processor can execute the program code 314 to perform all of the above-described operations and steps or others described herein.

According to the foregoing recitations of the embodiments of the invention, it can be seen that the method and the electronic device are capable of sensing touch force in the Z-axis direction by using the pressure sensor (e.g., a barometer). In addition, the electronic device is low-cost because no hardware changes are needed for a typical electronic device that already includes a processor and a pressure sensor.

Various aspects of the disclosure have been described above. It should be apparent that the teachings herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using another structure, functionality, or structure and functionality in addition to or other than one or more of the aspects set forth herein. As an example of some of the above concepts, in some aspects concurrent channels may be established based on pulse repetition frequencies. In some aspects concurrent channels may be established based on pulse position or offsets. In some aspects concurrent channels may be established based on time hopping sequences. In some aspects concurrent channels may be established based on pulse repetition frequencies, pulse positions or offsets, and time hopping sequences.

Those with skill in the art will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those with skill in the art will further appreciate that the various illustrative logical blocks, modules, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module"), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

In addition, the various illustrative logical blocks, modules, and circuits described in connection with the aspects disclosed herein may be implemented within or performed by an integrated circuit ("IC"), an access terminal, or an access point. The IC may comprise a general purpose processor, a digital signal processor (DSP), an application specific integrated circuit (ASIC), a field programmable gate array (FPGA) or another programmable logic device, discrete gate or transistor logic, discrete hardware components, electrical components, optical components, mechanical components, or any combination thereof designed to perform the functions described herein, and may execute codes or instructions that reside within the IC, outside of the IC, or both. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

It should be understood that any specific order or hierarchy of steps in any disclosed process is an example of a sample approach. Based upon design preferences, it should be understood that the specific order or hierarchy of steps in the processes may be rearranged while remaining within the scope of the present disclosure. The accompanying method claims present elements of the various steps in a sample order, and are not meant to be limited to the specific order or hierarchy presented.

The steps of a method or algorithm described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/processor (which may be referred to herein, for convenience, as a "processor") such that the processor can read information (e.g., code) from and write information to the storage medium. A sample storage medium may be integral to the processor. The processor and the storage medium may reside in an ASIC. The ASIC may reside in user equipment. In the alternative, the processor and the storage medium may reside as discrete components in user equipment. Moreover, in some aspects any suitable computer-program product may comprise a computer-readable medium comprising codes relating to one or more of the aspects of the disclosure. In some aspects a computer program product may comprise packaging materials.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An electronic device for sensing touch force, comprising:
    a display screen;
    a pressure sensor suitable for sensing a touch pressure applied to the display screen, sensing at least one touch force in a direction that is perpendicular to a plane of the display screen based on a pressure inside a membrane and generating at least one sensing signal responsive to the at least one touch force;
    a processor coupled to the pressure sensor and the display screen; and
    a memory operatively coupled to the processor;
    wherein the processor is configured to execute program code stored in the memory by:
    generating a control signal corresponding to the at least one sensing signal; and
    performing an operation according to the control signal,
    wherein the pressure sensor further comprises the membrane used for keeping air-tightness, and the pressure sensor is located in the membrane;
    wherein the pressure sensor is embedded between the display screen and a body of the electronic device, wherein the pressure sensor is disposed outside the body of the electronic device.

2. The electronic device for sensing touch force as claimed in claim 1, wherein before generating the control signal corresponding to the at least one sensing signal, the processor further executes:
    discriminating one of a plurality of levels of the sensing signal; and
    generating the control signal corresponding to the one of the plurality of levels.

3. The electronic device for sensing touch force as claimed in claim 2, wherein the performing the operation comprises one of the following:
controlling a three-dimensional (3D) depth of an object;
rendering a strength of the touch force;
refocusing the object; or
controlling a zoom ratio of the object.

4. The electronic device for sensing touch force as claimed in claim 1, wherein before generating the control signal corresponding to the at least one sensing signal, the processor further executes:
determining whether a number of times, duration of the at least one sensing signal, and strength of the at least one sensing signal satisfy one or more criteria; and
generating the control signal in response to a determination that the number of times, the duration, and the strength of the at least one sensing signal satisfies the one or more criteria.

5. The electronic device for sensing touch force as claimed in claim 4, wherein the performing the operation comprises one of the following:
making an emergency call;
unlocking the display screen;
capturing an image; or
performing an audio function.

6. A method for sensing touch force, used in an electronic device, comprising:
sensing, by a pressure sensor suitable for sensing a touch pressure applied to a display screen of the electronic device, at least one touch force in a direction that is perpendicular to a plane of the display screen of the electronic device based on a pressure inside a membrane and generating at least one sensing signal responsive to the at least one touch force; and
generating, by a processor of the electronic device, a control signal corresponding to the at least one sensing signal, and performing an operation according to the control signal,
wherein the pressure sensor comprises the membrane used for keeping air-tightness, and the pressure sensor is located in the membrane
wherein the pressure sensor is embedded between the display screen and a body of the electronic device, wherein the pressure sensor is disposed outside the body of the electronic device.

7. The method for sensing touch force as claimed in claim 6, wherein the pressure sensor is attached to a shell of the electronic device, wherein the shell of the electronic device is disposed outside the body of the electronic device.

8. The method for sensing touch force as claimed in claim 6, wherein before generating the control signal corresponding to the at least one sensing signal, the method further executes:
discriminating one of a plurality of levels of the sensing signal; and
generating the control signal corresponding to the one of the plurality of levels.

9. The method for sensing touch force as claimed in claim 8, wherein the performing the operation comprises one of the following:
controlling a three-dimensional (3D) depth of an object;
rendering a strength of the touch force;
refocusing the object; or
controlling a zoom ratio of the object.

10. The method for sensing touch force as claimed in claim 6, wherein before generating the control signal corresponding to the at least one sensing signal, the method further executes:
determining whether a number of times, duration of the at least one sensing signal, and strength of the at least one sensing signal satisfy one or more criteria; and
generating the control signal in response to a determination that the number of times, the duration, and the strength of the at least one sensing signal satisfies the one or more criteria.

11. The method for sensing touch force as claimed in claim 10, wherein the performing the operation comprises one of the following:
making an emergency call;
unlocking the display screen;
capturing an image; or
performing an audio function.

12. An electronic device for sensing touch force, comprising:
a display screen;
a pressure sensor configured to sense at least one touch force in a direction that is perpendicular to a plane of the display screen based on a pressure inside a membrane and generating at least one sensing signal responsive to the at least one touch force;
a processor coupled to the pressure sensor and the display screen; and
a memory operatively coupled to the processor;
wherein the processor is configured to execute program code stored in the memory by:
generating a control signal corresponding to the at least one sensing signal; and
performing an operation according to the control signal,
wherein the pressure sensor further comprises the membrane used for keeping air-tightness, and the pressure sensor is located in the membrane;
wherein the pressure sensor is attached to a shell of the electronic device, wherein the shell of the electronic device is disposed outside a body of the electronic device; and
wherein the pressure sensor is embedded between the display screen and the body of the electronic device, wherein the pressure sensor is disposed outside the body of the electronic device.

* * * * *